United States Patent
Keyes

(10) Patent No.: US 6,602,232 B1
(45) Date of Patent: *Aug. 5, 2003

(54) OSTOMY SYSTEM WITH REPOSITIONABLE POUCH

(75) Inventor: Denis E. Keyes, Yardley, GA (US)

(73) Assignee: E.R. Squibb & Sons, Inc., Princeton, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 39 days.

This patent is subject to a terminal disclaimer.

(21) Appl. No.: 08/390,180

(22) Filed: Feb. 17, 1995

(51) Int. Cl.[7] .................................................. A61F 5/44
(52) U.S. Cl. ....................................... 604/344; 604/338
(58) Field of Search ................................... 604/332–345

(56) References Cited

U.S. PATENT DOCUMENTS

| | | | | | |
|---|---|---|---|---|---|
| 4,701,169 | A | * | 10/1987 | Steer | 604/338 |
| 4,890,608 | A | * | 1/1990 | Steer | 604/332 |
| 4,894,058 | A | * | 1/1990 | Jensen | 604/332 |
| 5,496,296 | A | * | 3/1996 | Holmberg | 604/344 |

* cited by examiner

Primary Examiner—John G. Weiss
Assistant Examiner—Dennis Ruhl
(74) Attorney, Agent, or Firm—Stuart E. Krieger

(57) ABSTRACT

The ostomy system with mounting wafer and repositionable pouch includes a resealable tape provided on one of the system members and a releasable film provided on the other system member. In a preferred embodiment of the invention the resealable tape is located on a faceplate of the pouch and the releasable film is located on the body-side mounting wafer. The pouch is thus secured to the body-side mounting wafer by engaging the resealable tape with the releasable film. The resealable tape and the releasable film coupling arrangement permit repeated removal of the pouch from the body-side mounting wafer and repeated resecurement of the pouch to the mounting wafer. The pouch can thus be repositioned relative to the mounting wafer even after the pouch has been worn for a day.

14 Claims, 4 Drawing Sheets

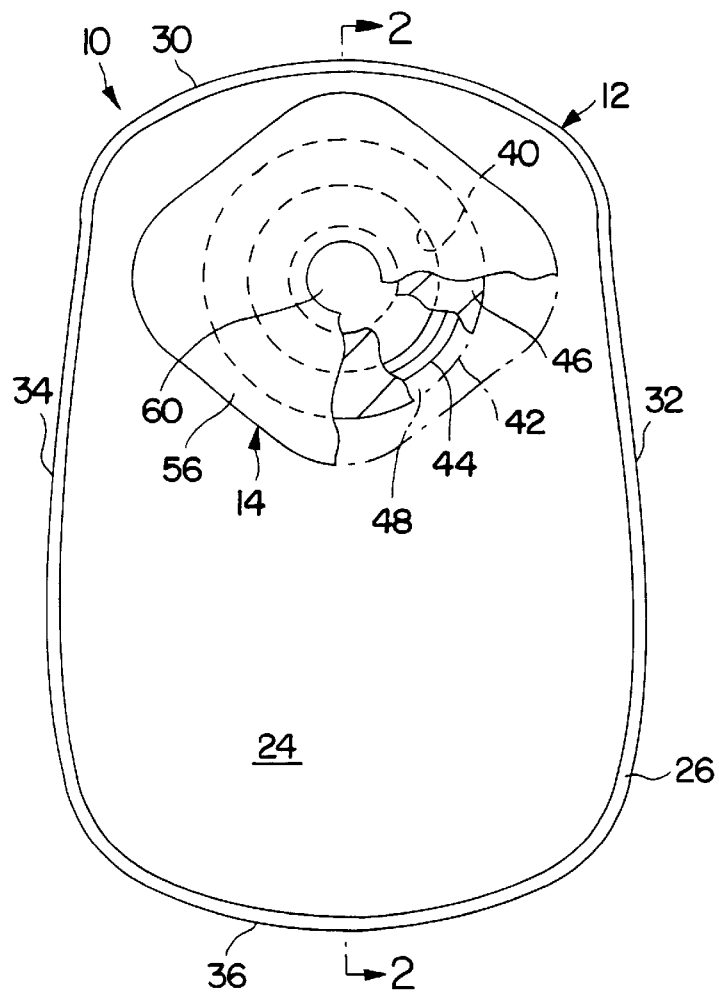
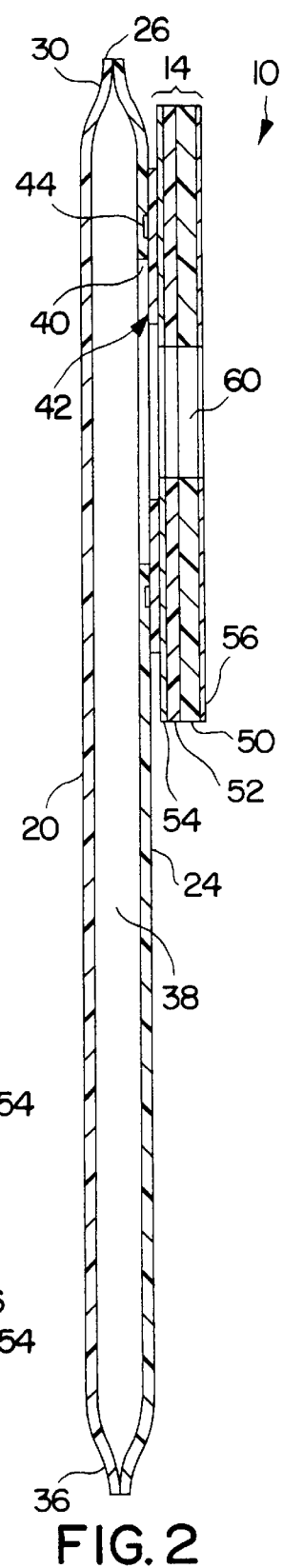
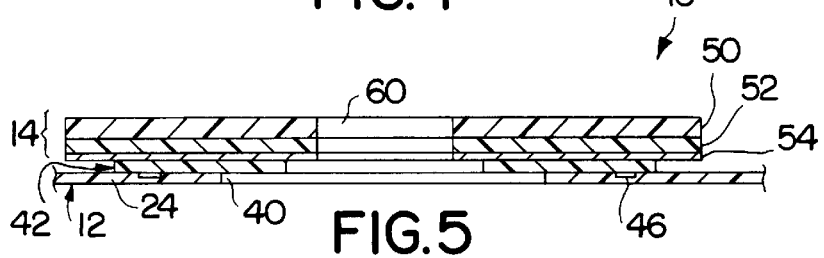
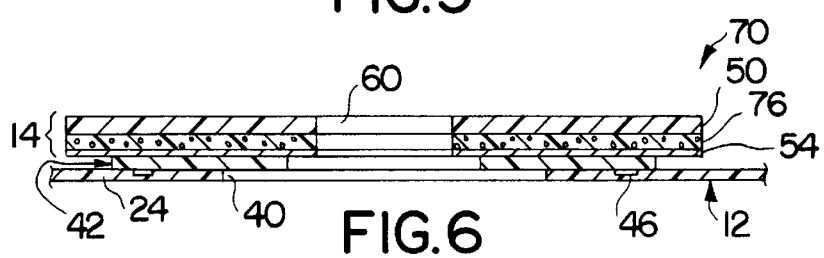
FIG. 1
FIG. 2
FIG. 5
FIG. 6

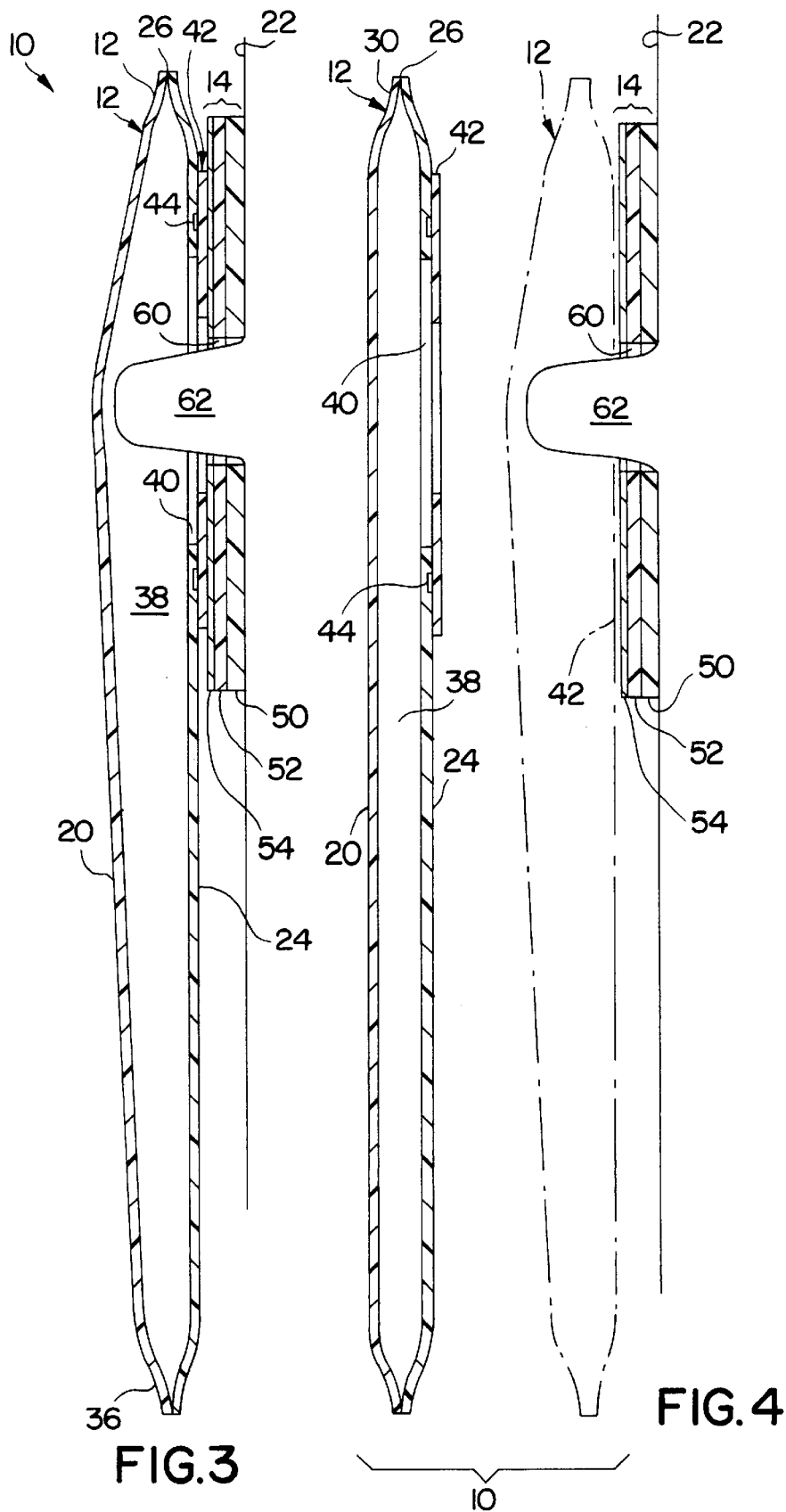

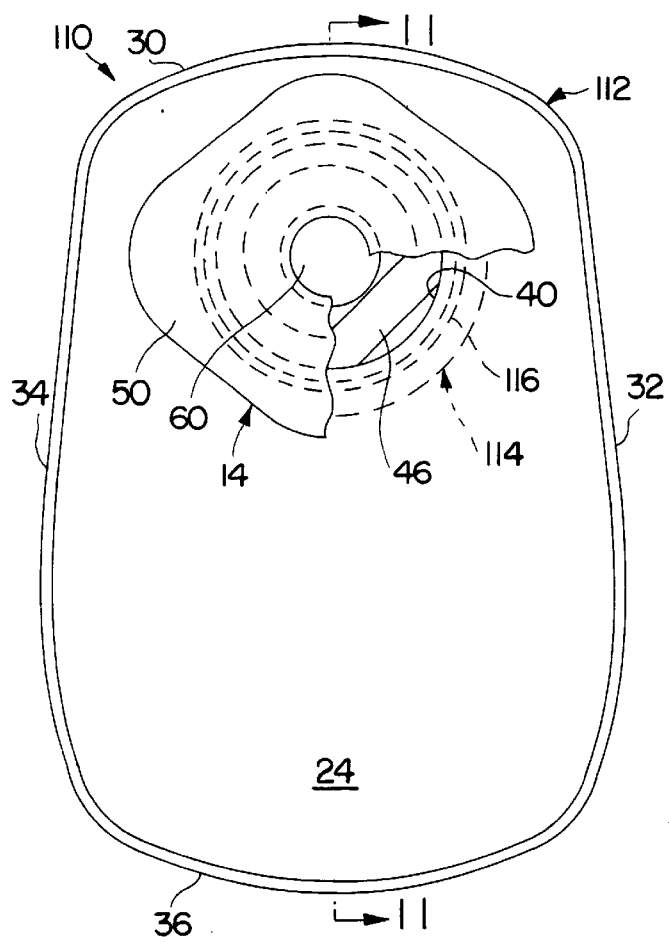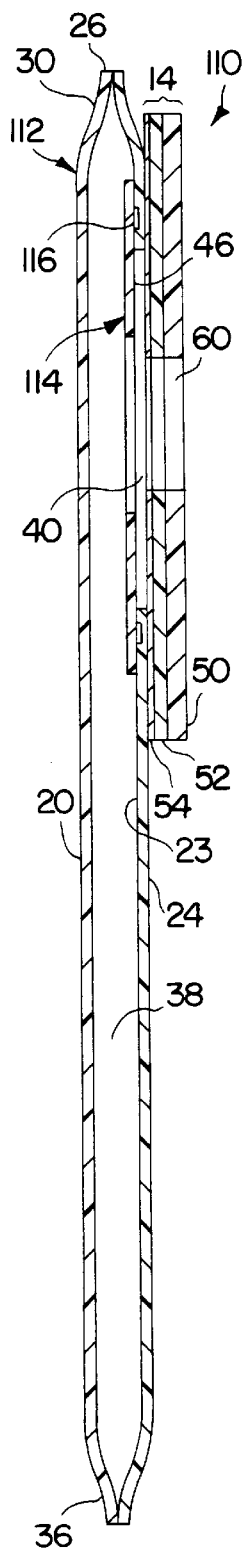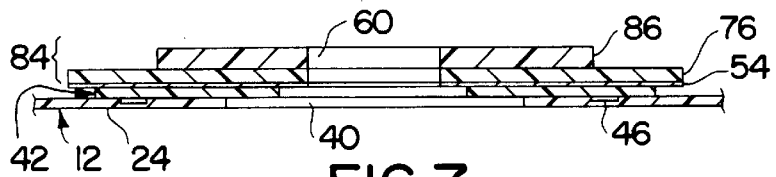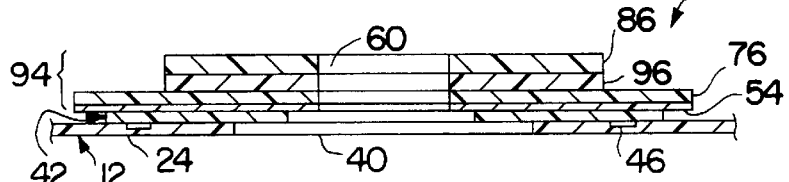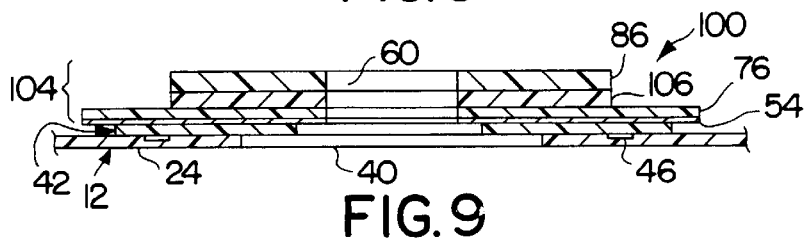

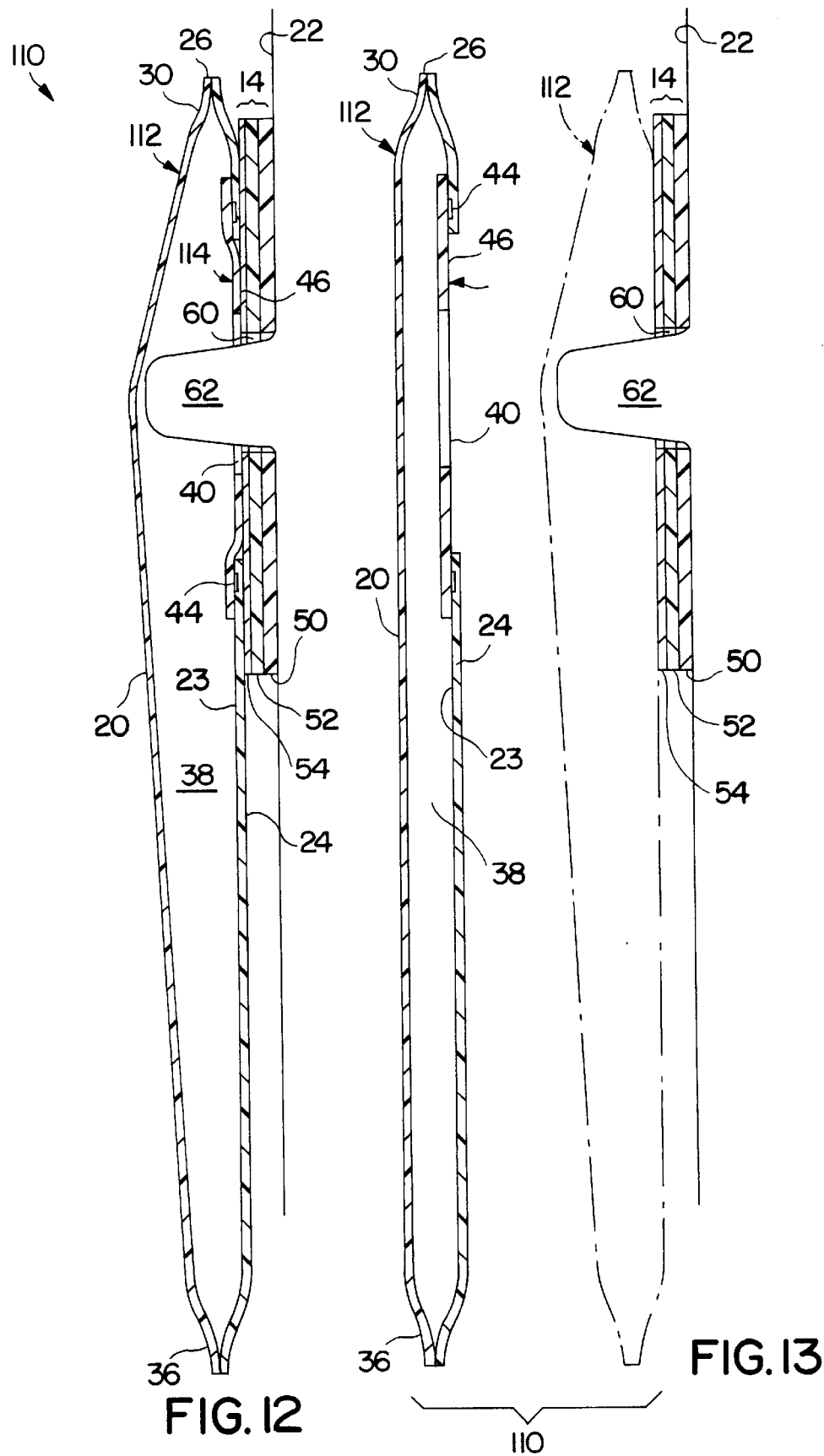

OSTOMY SYSTEM WITH REPOSITIONABLE POUCH

BACKGROUND OF THE INVENTION

This invention is directed to ostomy systems, and more particularly to a novel ostomy system that permits repeated removal of an adhesively installed ostomy pouch to permit repositioning of the pouch around the stoma.

Ostomy systems with adhesive coupling devices for securing an ostomy pouch around a stoma are shown in European Patent Application Publication 0 611 122 A1. After an ostomy pouch has been adhesively secured around a stoma, it is often desirable to make a further readjustment of the pouch position. However, it is well known that removal of an adhesively secured pouch from its position around a stoma can cause wrinkling or kinks in the faceplate of the pouch that includes the adhesive coupling member. Pouch removal can also cause wrinkling and kinks in a body-side mounting wafer that surrounds the stoma and forms a landing surface for the pouch faceplate when the pouch is adhesively secured to the abdominal area.

Removal and resecurement of an adhesively mounted closed-end pouch after the pouch has been worn for at least a day is especially troublesome since the mounting wafer landing surface for the pouch does not usually remain flat and smooth after a full day's wear. Readherence of the pouch to a non-smooth landing surface is likely to produce gaps or channels at the adhesive interface between the pouch faceplate and the body-side mounting wafer. Such gaps are detrimental to the integrity of the seal between the pouch and wafer, and can provide a path for undesirable leakage of vapor and material from the pouch.

Thus, an ostomy system which has leaks at the interface between the pouch and the body-side wafer due to repositioning of the pouch may require complete replacement of the entire system before it has been used for the normal time duration.

It is also common practice for a user to have assistance in placing or positioning a pouch on the abdomen in order to ensure that the pouch is satisfactorily positioned around the stoma. However, if assistance is not available when needed, the user may proceed to install the ostomy pouch without assistance, thereby risking unsatisfactory positioning and a need for readjustment of the pouch position.

The risk of wrinkle formation at the interface between an adhesively secured pouch and a body-side wafer because of a prospective need for repositioning of the pouch can discourage use of adhesively secured pouches, even though adhesive coupling is generally less bulky than mechanical coupling devices.

It is thus desirable to provide an ostomy system that permits easy removal and repositioning of an adhesively secured pouch without damaging the pouch faceplate or the mounting wafer and without compromising the leak-tight securement of the pouch during such repositioning.

OBJECTS AND SUMMARY OF THE INVENTION

Among the several objects of the invention may be noted the provision of a novel ostomy system, a novel ostomy system with a repositionable ostomy pouch, a novel ostomy system wherein the pouch is adhesively secured and repositionable without compromising a leak-tight seal between the pouch and a body-side wafer, a novel ostomy system wherein an installed body-side wafer remains substantially flat and smooth to provide a flat landing zone around the stoma, even after the pouch is removed from the installed wafer, a novel ostomy system wherein a stiffening member is provided on a body-side wafer to minimize the formation of wrinkles or folds on an installed wafer during repositioning of a previously installed ostomy pouch, a novel ostomy system wherein an ostomy pouch includes a refastenable adhesive member, and a novel method of repositioning an ostomy pouch around a stomal opening.

Other objects and features of the invention will be in part apparent and in part pointed out hereinafter.

In accordance with the invention, the ostomy system includes a repositionable pouch, which can be closed-end or drainable, and a body-side mounting wafer. The pouch comprises an envelope formed of flexible plastic sheet material that defines a chamber for collection of body waste from the stoma. A waste inlet opening is formed in the pouch to receive waste material that passes from the stoma into the collection chamber. Coupling means for securing the pouch to the body-side mounting wafer are provided on the pouch envelope at the waste inlet opening. The body-side mounting wafer has a stomal opening and an adhesive layer on one side for securement of the wafer to the body surface around the stoma. An opposite side of the wafer is engageable with the pouch coupling means.

The ostomy system coupling means include a resealable tape and a releasable film, one of which is provided on the pouch and the other of which is provided on the body-side mounting wafer.

In a preferred embodiment of the invention, the resealable tape is provided on the pouch and the releasable film is provided on the body-side mounting wafer. Thus the pouch can be secured to the wafer when the resealable tape engages the releasable film. The releasable film and the resealable tape permit repeated removal of the pouch from the wafer and repeated resecurement and/or replacement of a closed-end pouch to the wafer.

Under this arrangement the pouch can be easily repositioned on the body-side wafer, even after the pouch has been worn for a day.

The ostomy system also includes a support means disposed behind the releasable film to inhibit the formation of wrinkles on the releasable film and help keep the film flat and smooth. By maintaining the releasable film flat and smooth, leak-tight seals are obtainable between the pouch and the wafer, even when the pouch is repositioned several times on the body-side wafer.

A stiffening member can also be provided behind the resealable tape of the pouch coupling member to facilitate application of the pouch to the body-side wafer.

In several embodiments of the invention the resealable tape of the pouch is mounted on an outside surface of the pouch envelope. In other embodiments of the invention the resealable tape is mounted on an inside surface of the pouch envelope, such that exposed portions of the resealable tape are bordered by the pouch side-wall.

In some embodiments of the invention the support means of the body-side wafer are coextensive with the releasable film and a body-side adhesive. In other embodiments of the invention the support means include two support members, one of which is of smaller extent than the releasable film.

The faceplate of the pouch, which includes the pouch coupling member, can be heat-welded or adhesively bonded to a wall of the pouch.

The invention also includes a method of repositioning an ostomy pouch around a stomal opening, including the securing of a body-side wafer around the stomal opening, providing the mounting wafer with a landing surface formed of releasable film and providing the ostomy pouch with an adhesive coupling having an exposed resealable tape for engagement with the releasable film of the body-side mounting wafer to permit repeated removal, replacement and resecurement of the pouch to the mounting wafer.

The invention accordingly comprises the constructions and method hereinafter described, the scope of the invention being indicated in the claims.

DESCRIPTION OF THE DRAWINGS

In the accompanying drawings,

FIG. 1 is a plan view of an ostomy system including an ostomy pouch and a body-side wafer that incorporate one embodiment of the invention;

FIG. 2 is a sectional view thereof, taken on the line 2—2 of FIG. 1;

FIG. 3 is a sectional view similar to FIG. 2, showing the ostomy system on an abdominal wall in alignment with a stoma;

FIG. 4 is a view similar to FIG. 3, showing the ostomy pouch detached from the body-side wafer prior to repositioning of the pouch against the wafer;

FIG. 5 is a fragmentary sectional view thereof;

FIGS. 6–9 are fragmentary sectional views of further embodiments of the invention;

FIG. 10 is a plan view of an ostomy system including an ostomy pouch and a body-side wafer that incorporate a further embodiment of the invention;

FIG. 11 is a sectional view thereof, taken on the line 11—11 of FIG. 10;

FIG. 12 is a view similar to FIG. 11, showing the ostomy system on an abdominal wall in alignment with a stoma; and FIG. 13 is a view similar to FIG. 12, showing the ostomy pouch detached from the body-side wafer prior to repositioning of the pouch against the wafer.

Corresponding reference characters indicate corresponding parts throughout the several views of the drawings.

DETAILED DESCRIPTION OF THE INVENTION

An ostomy system incorporating one embodiment of the invention is generally indicated by the reference number 10 in FIG. 1.

The ostomy system 10 includes a pouch 12 and a body-side mounting wafer 14, shown in separated position in FIG. 4. The pouch 12, which is expandable, is formed of an envelope of suitable flexible thermoplastic material known in the art of pouch construction, such material being impermeable to gas and water.

The pouch 12 includes a front wall 20 that faces away from an abdominal surface 22 (FIG. 8), and a rear wall 24 that confronts the abdomen 22. The front and rear walls 20 and 24 of the pouch 12 are joined together by a peripheral thermoweld 26. The pouch 12 further includes a top portion 30 with rounded corners and opposite side portions 32 and 34 that diverge slightly from the top portion 30 to a bottom portion 36. The pouch envelope thus defines a waste collection chamber 38.

A waste inlet opening 40 having a diameter of approximately two inches is formed in the rear wall 24 nearer the top portion 30 than the bottom portion 36. The waste inlet opening 40 communicates with the collection chamber 38 and is bordered by a washer-shaped adhesive faceplate 42 attached to the rear wall 24 by an annular thermoweld 44. The faceplate 42 is preferably formed of a resealable tape 46 which can be a two-sided adhesive tape of the type used in the refastenable tape closure system 9920 and/or 9835 manufactured by the 3M Company of Minneapolis, Minn. The resealable tape 46 includes a hypo-allergenic acrylic pressure-sensitive adhesive on ethylene vinyl acetate or polyethylene tape with silicone release paper. The faceplate 42 has an inner diameter of approximately two inches and an outer diameter of approximately three and one-half inches.

A stiffening member 48 (FIG. 1), preferably formed of elastomeric material, can be laminated to the back of the resealable tape 46 before the faceplate 42 is adhered to the pouch. The stiffening member 48 reduces flexibility of the faceplate 42 and facilitates application and removal of the pouch 12 from the mounting wafer 14. Preferably the stiffening member 48 is a plasticized flexible polyvinyl chloride sheet material 0.010"–0.080" thick. For purposes of simplicity, the faceplate 42, as shown in Figures other than FIG. 1, will be understood to incorporate the stiffening member 48.

If desired, the faceplate 42 can be adhered rather than heat welded to the pouch wall 24, as by applying pressure-sensitive adhesive to the non-coated side to permit an adhesive bond between the faceplate 42 and the rear wall 24. Although not shown, a silicone release paper covers the exposed surface of the faceplate 42 to protect the adhesive surface of the tape 46 prior to use of the pouch 12.

The body-side mounting wafer 14 is generally square with rounded corners and has a central opening 60 with a diameter of approximately one-half to one-and-three-quarter inches. The wafer 14 is sized to extend beyond the periphery of the faceplate 42 and includes a first layer 50. Preferably the layer 50 is formed of a hydrocolloid adhesive, approximately 0.030 to 0.080 inches thick, such as the type sold under the trademark Stomahesive® or Durahesive® by Bristol-Myers Squibb Company of New York, N.Y. A support layer 52, of substantially identical size as the layer 50, is laminated to the layer 50 and facilitates application of the pouch 12 to the wafer 14. The support layer 52 is formed of a plasticized, flexible polyvinyl chloride sheet material approximately 0.010 to 0.080 inches thick.

A release film 54, approximately 0.003 inches thick, also substantially identical in size to the layer 50, is laminated to the support layer 52 to function as a target or landing area for the refastenable faceplate 42 of the pouch 12. Preferably the release film 54 is a single-coated, pressure-sensitive adhesive medical tape of the type sold by the 3M Company of St. Paul, Minn., under the designation of 3M Release Tape 9921, or Tegaderm, which has a controlled release surface treatment. The release film 54 engages the adhesive faceplate 42 of the pouch 12 for attachment of the pouch 12 to the wafer 14.

The release film 54 permits removal of the pouch faceplate 42 from the body-side wafer 14 after prior pouch attachment such that the pouch 12 can be repositioned on the wafer 14. Removal and reattachment or replacement of the pouch 12 can be accomplished numerous times. Since contours can exist around the stomal area, the landing zone on the release film 54 may not remain flat and smooth, especially after the body-side wafer 14 is worn for more than a day. The support layer 52 inhibits the formation of wrinkles on the release film 54, helping to keep the film 54 flat and smooth. It has been found that a leak-tight seal is obtainable even after numerous repositionings or replacements of the pouch 12 on the wafer 14.

A known silicone release paper 56 (FIG. 2) is provided on the outside of the adhesive layer 50 to protect the layer 50 until the body-side mounting wafer 14 is ready for installation on the abdominal surface 22.

In using the ostomy system 10, the release paper 56 is removed from the body-side mounting wafer 14. The wafer 14 is secured to the abdominal wall at the layer 50 such that an opening 60 in the mounting wafer 14 aligns with a stoma 62. Any protective covering (not shown) provided on the release film 54 is also removed to expose the landing surface of the release film 54.

The silicone release paper 56 is removed from the resealable adhesive 46 of the faceplate 42. The pouch 12 is installed on the abdomen by joining the adhesive surface 46 of the faceplate 42 to the release film 54 such that the pouch opening 40 is substantially coaxial with the wafer opening 60 in the manner shown in FIG. 8.

In some instances the desired coaxial relationship between the pouch opening 40 and the wafer opening 60 is not obtained, or the pouch opening 40 is not comfortably positioned around the stoma 62. Thus it becomes necessary to reposition the pouch 12 relative to the mounting wafer 14.

The release film 54 of the wafer 14 permits easy removal of the adhesive layer 46 of the pouch faceplate 42 from the wafer 14 to separate the pouch 12 from the wafer 14 in the manner shown in FIG. 4. The pouch 12 can then be repositioned relative to the wafer 14.

The stiffening layer 48 and the support layer 52 help provide substantially smooth wrinkle-free surfaces on the wafer 14 and the pouch faceplate 42 when the pouch 12 is resecured to the wafer 14 during repositioning of the pouch 12.

Once the pouch 12 is resecured to the wafer 14 in a manner similar to that previously described, further adjustment, if desired, can still be made. Thus it is possible to remove and reposition or replace the pouch several times when needed.

Another embodiment of the ostomy system is generally indicated by the reference number 70 in FIG. 6. The ostomy system 70 includes a body-side wafer 74 that differs from the wafer 14 of the system 10 by replacement of the support layer 52 of the system 10 with a support layer 76. The support layer 76 is preferably formed of polyethylene closed-cell foam with pressure-sensitive adhesive that is approximately 0.015 to 0.050 inches thick, to laminate to the hydrocolloid adhesive layer 50. The system 70 is otherwise similar to the system 10 and is used in a manner as previously described for the system 10.

An ostomy system incorporating a further embodiment of the invention is generally indicated by the reference number 80 in FIG. 7. The ostomy system 80 includes a body-side wafer 84 that differs from the wafer 74 of the ostomy system 70 by replacement of the body-side adhesive layer 50 with a body-side adhesive layer 86. The layer 86 is formed of the same material as the layer 52 but is of a smaller width than the layer 52 by, for example, approximately onehalf inch on each side. The system 80 is otherwise similar to the system 10 and is used in a manner similar to that previously described for the system 10.

A further embodiment of the ostomy system is generally indicated by the reference number 90 in FIG. 8. The ostomy system 90 includes a body-side wafer 94 that differs from the wafer 84 of the system 80 by inclusion of an additional support layer 96 provided between the layers 76 and 86. The support layer 76 is formed of elastomeric material, such as polyvinyl chloride, that is approximately 0.010 to 0.080 inches thick, and has substantially the same outer dimensions as the layer 86. The system 90 is otherwise similar to the system 10 and is used in a manner similar to that previously described for the system 10.

An ostomy system incorporating another embodiment of the invention is generally indicated by the reference number 100 in FIG. 9. The ostomy system 100 includes a body-side wafer 104 that differs from the wafer 94 by replacement of the support layer 96 in the system 90 with a support layer 106. The support layer 106, which is approximately 0.010 to 0.050 inches thick, is preferably formed of Silipos material, manufactured by Silipos Inc. of New York, N.Y. The layer 106 has substantially the same outside dimensions as the layer 86. The system 100 is otherwise similar to the system 10 and is used in a manner similar to that previously described for the system 10.

An ostomy system incorporating still another embodiment of the invention is generally indicated by the reference number 110 in FIG. 11.

The ostomy system 110 includes a pouch 112 and a body-side mounting wafer 14, shown in separated position in FIG. 13.

The pouch 112 includes a faceplate 114 similar to the faceplate 42 of the system 10. However, the faceplate 114 is adhered to an inner surface 23 of the rear wall 24 by an annular thermoweld 116 or a pressure-sensitive adhesive. Thus a portion of the faceplate 114 projects into the pouch opening 40, as most clearly shown in FIG. 13. The surface of the faceplate 114 is constituted of the resealable tape 46, which is engageable with the layer 54 of the wafer 14.

As noted with the system 10, the faceplate 114 can be adhered rather than heat-welded to the pouch wall.

In using the ostomy system 110, the wafer 14 is secured to the abdominal wall 22 in a manner previously described for the system 10. The pouch 112 is prepared for engagement with the body-side mounting wafer 14 by removing a silicone release paper (not shown) applied over the resealable tape 46 to protect the surface of the tape until engagement is to be accomplished.

The pouch 112 is installed on the abdomen by joining the adhesive surface 46 of the faceplate 114 to the release film 54 of the wafer 14 in the manner shown in FIG. 12.

If desired, the pouch 112 can be repositioned relative to the wafer 14 in a manner similar to that previously described for the system 10.

In other embodiments of the ostomy system that incorporate the present invention, the body-side mounting wafer 14 of the system 110 can be replaced by the mounting wafers 74, 84, 94 or 104. Thus the pouch 112 can be combined with any of the five mounting wafer arrangements previously described to achieve the objectives of the invention.

Some advantages of the present invention evident from the foregoing description include an ostomy system that permits easy removal of a pouch from a body-side mounting wafer without the need for mechanical coupling arrangements or bulky latching devices. The resealable adhesive securement of the pouch to the body-side mounting wafer also permits easy repositioning of the pouch around the stoma to provide the user with an option for adjusting the position of the pouch around the stoma. Such adjustment or repositioning and replacement of the pouch is obtainable without compromising the integrity of the seal between the pouch and the body-side wafer despite repeated removal and repositioning of the pouch. Thus an adhesively secured pouch that is removed because of a positioning problem need not be discarded, but can be reinstalled and used until the pouch is ready for disposal. The repositioning capability of the present invention eliminates a common source of frustration to the user of adhesively secured ostomy pouches.

In view of the above, it will be seen that the several objects of the invention are achieved and other advantageous results attained.

As various changes can be made in the above constructions and method without departing from the scope of the invention, it is intended that all matter contained in the above description or shown in the accompanying drawings shall be interpreted as illustrative and not in a limiting sense.

What is claimed is:

1. An ostomy system comprising:
   a) an ostomy pouch including a pouch envelope formed of flexible plastic material defining a waste collection chamber for body waste that passes through a stoma, a waste inlet opening formed in said envelope for passage of waste material from said stoma to said collection chamber, a flexible annular adhesive pouch coupling member on said envelope at said waste inlet opening, said pouch coupling member having a resealable tape;
   b) a body-side mounting wafer having a stomal opening, said mounting wafer being engageable with the coupling member of said pouch, said mounting wafer having one side with an adhesive layer for securement to a body surface around a stoma, and an opposite side with a releasable film permanently secured to said wafer for engagement with the resealable tape of said pouch coupling member, such that said pouch can be secured to said wafer when the resealable tape of the pouch coupling member engages the releasable film of the wafer, said releasable film extending from an inner periphery surrounding said stomal opening to an outer periphery, said releasable film and said resealable tape permitting repeated removal of said pouch from said wafer and repeated resecurement and replacement of said pouch to said wafer; and
   c) support means coextensive and underlying said releasable film for preventing wrinkling of any part of said releasable film.

2. The ostomy system as claimed in claim 1 wherein said adhesive layer and said releasable film are coextensive.

3. The ostomy system as claimed in claim 1 wherein said releasable film extends beyond the perimeter of said adhesive layer.

4. The ostomy system as claimed in claim 1 wherein said support means is formed of a material selected from the group consisting of polyvinyl chloride, and polyurethane closed-cell foam.

5. The ostomy system as claimed in claim 1 wherein said support means is disposed between said adhesive layer and said releasable film.

6. The ostomy system as claimed in claim 5 wherein said adhesive layer and said releasable film are coextensive and said support means is coextensive with said adhesive layer and said releasable film.

7. The ostomy system as claimed in claim 5 wherein said releasable film extends beyond the perimeter of said adhesive layer.

8. The ostomy system as claimed in claim 7 wherein said support means is coextensive with said adhesive layer.

9. The ostomy system as claimed in claim 7 wherein said support means include a pair of support layers disposed between said adhesive layer and said releasable film.

10. The ostomy system as claimed in claim 9 wherein one of said support layers is coextensive with the adhesive layer and the other said support layer is coextensive with the releasable film.

11. The ostomy system as claimed in claim 1 wherein said pouch coupling member is mounted on an outside surface of said pouch envelope.

12. The ostomy system as claimed in claim 11 wherein said pouch coupling member includes a support member disposed between said resealable tape and the outside surface of said pouch envelope.

13. The ostomy system as claimed in claim 1 wherein said pouch coupling members is mounted on an inside surface of said pouch envelope.

14. The ostomy system as claimed in claim 12 wherein said support member is disposed behind said resealable tape.

* * * * *